United States Patent [19]

LoPresti et al.

[11] Patent Number: 5,387,520
[45] Date of Patent: Feb. 7, 1995

[54] TREATMENT OF TUMOR CELLS IN VITRO WITH NEUROTROPHIC FACTORS AND CELL PROLIFERATION INHIBITORS

[75] Inventors: Patrizia LoPresti, Stony Brook, N.Y.; Wojciech Poluha, Shrewsbury, Mass.; Dorota K. Poluha, Shrewsbury, Mass.; Alonzo H. Ross, Shrewsbury, Mass.

[73] Assignee: Worcester Foundation for Experimental Biology, Shrewsbury, Mass.

[21] Appl. No.: 936,923

[22] Filed: Aug. 27, 1992

[51] Int. Cl.$^6$ .................... A61K 37/02; A61K 37/36; C07H 15/00
[52] U.S. Cl. ................ 435/240.2; 530/399; 514/2; 514/8; 514/12; 435/240.1; 435/243; 435/244; 435/245
[58] Field of Search ................ 530/399; 514/12, 2, 514/8; 536/22.1; 435/240.1, 240.2, 243, 244, 245

[56] References Cited

U.S. PATENT DOCUMENTS

| | | | |
|---|---|---|---|
| 4,803,201 | 2/1989 | Ratcliffe | 514/729 |
| 5,008,252 | 4/1991 | Cheng et al. | 514/50 |
| 5,039,710 | 8/1991 | Ratcliffe | 514/729 |

OTHER PUBLICATIONS

Saneto et al. "Neuronal & Glued Cells: Cell Culture of the CIS" in *New Chemistry: A Practical Approach*, Turner A. J. (ed.), Ill. Press, (England), 1987.
LoPristi et al., *Cell Growth & Diff.*, 3:627-635 (1992).
Pardee *Curr. Opin. Cell Biol.*, 4:186-191 (1992).
Snyder, *Nature*, 350:195-196 (1991).
Hohn et al., *Nature*, 344:339-341 (1990).
Stuiver et al., *FEBS Lett.*, 282(1):189-92 (1991).
Greene et al., (1976), *Proc. Natl. Acad. Sci. USA*, 73:2424-2428.
Evans et al., (1980), *Cancer*, 45:833-839.
Knudson, (1980), *New Eng. Journ. of Med.*, 302:1254-1256.
Huberman, (1981), *Cell*, 23:647-648.

Griffin et al., (1982), *Exp. Hematol.*, 10:774-781.
Iliakis et al., (1982), *Int. J. Radiat. Biol.*, 42:417-434.
Sonnenfeld et al., (1982), *Journal of Neurosci. Res.*, 8:375-391.
Smith et al., (1983), *Biochimica et Biophysica Acta*, 739:17-26.
Vinores et al., (1983), *Journal of Neursci. Res.*, 9:81-100.
Chou et al., (1985), *Cell Tissue Kinetics*, 18:387-397.
Lillien et al., (1985), *Nature*, 317:632-634.
Johnson et al., (1986), *TINS*, 1:33-37.
Lorenzo et al., (1986), *Journ. of Clin. Invest.*, 77:1897-1902.
Goretzki et al., (1987), *Surgery*, 102:1035-1042.
Jensen, (1987), *Developmental Biol.*, 120:56-64.
Levi-Montalcini, (1987), *Science*, 237:1154-1162.
Packard, (1987), *Proc. Natl. Acad. Sci. USA*, 84:9015-9019.
Rohrer et al., (1987), *J. Neurosci.*, 7:3739-3748.
Turner et al., (1987), *Nature*, 328:131-136.

(List continued on next page.)

*Primary Examiner*—Garnette D. Draper
*Assistant Examiner*—Shelly Guest Cermak
*Attorney, Agent, or Firm*—Lappin & Kramer

[57] ABSTRACT

Disclosed are methods and compositions for treating neuroblastoma cells. The methods include contacting the neuroblastoma cells with a neurotrophic factor and less than a lethal dose of an inhibitor of cell proliferation for about 1 to 15 days, and then maintaining the neuroblastoma cells in contact with the neurotrophic factor for an additional 1 to 15 days. The composition includes a neurotrophic factor such as the neurotropin, nerve growth factor, and an inhibitor of cell proliferation such as aphidicolin, thymidine, or hydroxyurea. Also disclosed are methods for inducing the remission or differentiation of, or eliminating, neuroblastoma cells.

17 Claims, 7 Drawing Sheets

OTHER PUBLICATIONS

Jensen et al., (1958), *Mol. Cell Biol.*, 8:3964–3968.
Kawahara et al., (1988), *Develop. Biol.*, 132:73–80.
Martin et al., (1988), *J. Cell Biol.*, 106:829–844.
McConnell, (1988), *Journ. of Neurosci.*, 8(3):945–974.
Sugimoto, (1988), *Journal of Biol. Chem.*, 263:12102–12108.
Ernsberger et al., (1989), *Neuron.*, 2:1275–1284.
Marushige et al., (1989), *Anticancer Res.*, 9:1729–1736.
Azar et al., (1990), *Cell Growth and Differentiation*, 1:421428.
Cattaneo et al., (1990), *Nature*, 347:762–765.
Chen et al., (1990), *Cell Growth and Differentiation*, 1:79–85.
DiCiccio-Bloom et al., (1990), *Journal of Cell Biol.*, 110:2073–2086.
Cattaneo et al., (1991), *TINS*, 14:338–340.
Dinsmore et al., (1991), *Cell*, 64:817–826.
George et al., (1991), *Proc. Natl. Acad. Sci. USA*, 88:11–15.
Jensen et al., (1992), *J. Biol. Chem.*, 267:19325–19333.

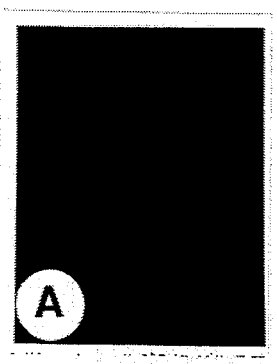
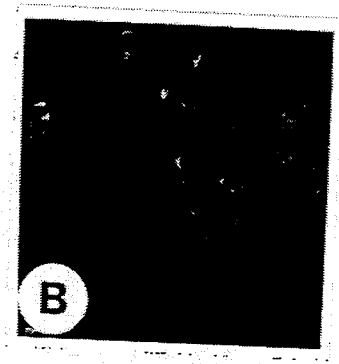
FIG. 5A    FIG. 5B
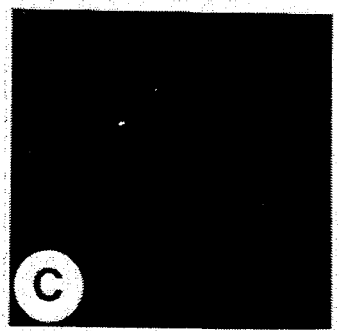
FIG. 5C
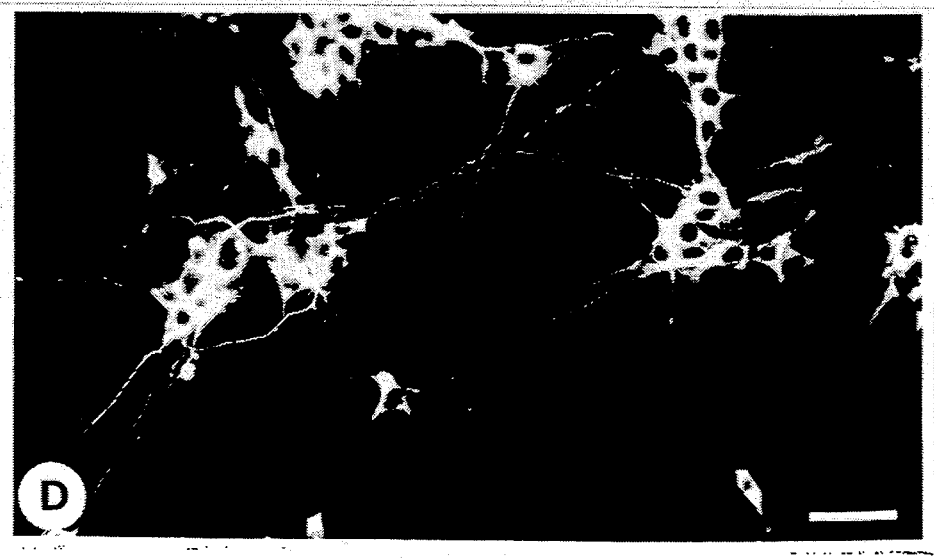
FIG. 5D

TREATMENT OF TUMOR CELLS IN VITRO WITH NEUROTROPHIC FACTORS AND CELL PROLIFERATION INHIBITORS

FIELD OF THE INVENTION

The technical field of this invention is tumor chemotherapy and in particular, novel methods and compositions for treating tumors. More specifically, this invention relates to the treatment of neuroblastomas with cell differentiation factors and inhibitors of cell proliferation.

BACKGROUND OF THE INVENTION

The nervous system is derived from multipotential precursor cells that show a closely regulated inverse relationship between cell proliferation and differentiation (Cattaneo and McKay (1991) *TINS* 14: 338–340). In the central nervous system, these precursor cells commit to a specific differentiation pathway shortly after the last mitosis (McConnell (1988) *J. Neurosci.* 8: 945–974; Turner and Cepko (1987) *Nature* 328: 131–136). In the peripheral nervous system, sensory neurons differentiate following withdrawal from the cell cycle (Rohrer and Thoenen (1987) *J. Neurosci.* 7: 3739–3748), but sympathetic neurons begin to differentiate, expressing neurotransmitter systems and extending short neurites, while still mitotically active (DiCicco-Bloom et al. (1990) *J. Cell Bio.* 110: 2073–2086). The molecular basis of the coupling between neuronal differentiation and cell proliferation is a problem of current interest.

The coupling between neuronal differentiation and cell proliferation also is relevant to the etiology of neural tumors, such as neuroblastoma. Neuroblastoma is one of the most common pediatric solid tumors, frequently occurring in infancy with the primary lesion in the adrenals and sympathetic chain (Voute (1984) "Neuroblastoma in: *Clinical Pediatric Oncology*" (W. W. Sutow, D. J. Fernback and T. J. Vietti, ed.) pp 559–587). This tumor is difficult to treat as common modes of chemotherapy have harsh side effects on normal infant tissue. Interestingly, neuroblastomas are noted for their ability to undergo spontaneous regression or maturation to benign ganglioneuromas (Evans et al. (1980) *Cancer* 45: 833–839). The similarity of neuroblastoma cells to neuroblasts and their ability to spontaneously mature to a more benign form suggest that the disease may originate by a block of differentiation of a sympathetic precursor cell (Knudson and Meadows (1980) *New Engl. J. Med.* 302: 1254–1256). Hence, factors which promote the differentiation of proliferating neuroblastic cells are candidates for new therapeutic approaches. Due to the side effects of cancer therapy, there is great need for "natural" but highly-specific pharmaceutical treatments.

Nerve growth factor (NGF) is a 26,000-dalton polypeptide neurotrophic factor that mediates a variety of biological responses (Levi-Montalcini and Aloe (1987) *Science* 237: 1154–1162). NGF acts as a survival factor for sympathetic and sensory neurons both in vivo and in culture (Johnson et al. (1986) *Trends Neurosci.* 9: 33–37). NGF is a differentiation factor for pheochromocytoma cell line PC12 (Greene and Tischler (1976) *Proc. Natl. Acad. Sci. USA* 73: 2424–2428). The effects of NGF on cell division vary with cell type. PC12 cells nearly cease to divide after exposure to NGF (Greene and Tischler (1976) *Proc. Natl. Acad. Sci. USA* 73: 2424–2428). Fetal chromaffin cells (Lillien and Claude (1985) *Nature* 317: 632–634) divide several times in response to NGF before terminally differentiating. Neuronal precursor cells from embryonic striatum proliferate in response to NGF but only after exposure to basic fibroblast growth factor (Cattaneo and McKay (1990) *Nature* 347: 762–765).

The use of cell differentiation factors such as NGF alone, however, has proven insufficient for the effective treatment of neuroblastomas. First, the response of neuroblastoma cell lines to NGF varies (Azar et al. (1990) *Cell Growth Diff.* 1: 421–428; Chen et al. (1990) *Cell Growth Diff.* 1: 79–85; Sonnenfeld and Ishii (1982) *J. Neurosci. Res.* 8: 375–391). Neuroblastoma cell lines with amplified N-myc oncogene have little or no response to NGF. SHSY5Y and some other neuroblastoma cell lines with single-copy N-myc extend short, branched neurites in response to NGF (Chen et al. (1990) *Cell Growth Diff.* 1: 79–85). However, NGF does not slow the rate of proliferation of these cells, and the differentiation is reversible. Upon the removal of NGF, the neurites retract. The inability of neuroblastoma cells to terminally differentiate may be a critical factor in this disease (Azar et al. (1990) *Cell Growth Diff.* 1: 421–428). As described in the references discussed below, blockade of cell division, alone, does not appear to be sufficient to promote fiber outgrowth. On the other hand, the compound aphidicolin has been reported to enhance the differentiation of human cell lines. Aphidicolin is a steroid-like molecule isolated from fungi which reversibly inhibits DNA polymerase $\alpha$ and $\delta$ and blocks the cell cycle at $G_1/S$ (Huberman (1981) *Cell* 23: 647–648). Chou and Chervenick (*Cell Tissue Kinet.* (1985) 18: 387–397) reported that a low concentration (0.4 $\mu$M) of aphidicolin enhances the retinoic acid-induced differentiation of human leukemia cells. Jensen (*Dev. Biol.* (1987) 120: 56–64) found that SHSY5Y cells treated with NGF and a pulse of aphidicolin extend long neurites (greater than 300 $\mu$m) and irreversibly differentiate. A high, and lethal, concentration (30 $\mu$M) of aphidicolin was used by Jensen to select postmitotic SHSY5Y cells, resulting in considerable cell toxicity. Combining NGF and sublethal doses of aphidicolin to effect the growth of SHSY5Y cells and still provide beneficial results was not discussed until the present invention.

For example, Griffin et al. (*Exp. Haematology* (1982) 10: 774–781) monitored the effects of two specific inhibitors of DNA synthesis, cytosine arabinoside and aphidicolin, to determine whether the slowing of DNA polymerization can induce differentiation in HL-60 human leukemic promyelocytes. The results indicated that cytosine arabinoside and aphidicolin both induced cellular differentiation in HL-60 cells. The inhibition of DNA synthesis, and thereby of cellular replication, may permit cells to express genetic information that results in a differentiated phenotype. The normal balance between proliferation and differentiation which has been lost in myeloblastic leukemic cells may be partially restored by blocking proliferation with drugs such as cytosine arabinoside or aphidicolin. No recommendation as to specific methods to accomplish this goal for different cell lines is provided.

Sonnenfeld and Ishii (*J. Neurosci. Res.* (1982) 8: 375–391) investigated whether the response of cultured human neuroblastoma cells to NGF was altered in a manner consistent with the pattern of decreased sensitivity to normal growth regulators exhibited in other malignant transformed cell types. A number of cell lines were examined to assess the degree of variability in response between cell lines. Thus an altered response to NGF may be associated with human neuroblastoma. It is pointed out that regulation of neurite outgrowth and cellular growth or proliferation are separable in neuroblastoma. However, Sonnenfeld and Ishii failed to demonstrate that NGF reduced the growth rate or survival of any neuroblastoma cell line.

Chou and Chervenick (*Cell Tissue Kinetics* (1985) 18: 387-397) evaluated the relationships between replicative DNA synthesis and retinoic acid (RA)-induced differentiation of human promyelocytic leukemic (HL-60) cells with the use of aphidicolin. The addition of a sublethal concentration of aphidicolin (0.4 $\mu$M) in culture for three days suppressed DNA synthesis to a similar level of the resting stage in control cultures. DNA synthesis and cell proliferation was reactivated to the level observed in the growing stage of control cultures once aphidicolin was removed after three days in culture. The inhibitory effect of aphidicolin on DNA synthesis in both control cultures and RA-induced cell cultures appeared to be similar. However, no reactivation of DNA synthesis was observed after removal of aphidicolin on day 3 from RA-induced cell cultures. It was pointed out that cells accumulated in $G_1$ and early S phases of the cell cycle after exposure to aphidicolin with or without RA. Aphidicolin alone did not induce cells to differentiate. The rate of RA-induced cell differentiation in the presence of aphidicolin was similar to that of RA treated cultures in the absence of aphidicolin. It was suggested that the combined use of aphidicolin and RA may effectively inhibit leukemic cell proliferation without causing severe cytotoxicity and without interfering with RA induced cell differentiation. The viability of HL-60 cells was assessed through exposure to 0.2 $\mu$M retinoic acid and/or 0.4 $\mu$M aphidicolin in RPMI-FCS medium. Aphidicolin, when present, was removed from cells by washing with medium at day 3 after seeding. It was determined that treatment of leukaemic cells with aphidicolin for a period of one doubling of the cell numbers suppresses DNA replication without influencing RA-induced cell differentiation. The authors make no suggestion that aphidicolin may act together with a neurotrophic factor to enhance the differentiation potential of a neurotrophic factor.

Packard (*Proc. Natl. Acad. Sci. USA* (1987) 84: 9015-9019)reports that a synthetic nonapeptide fragment of thrombin inhibits the cellular motility in culture of a human melanoma subclone that possesses a high metatastic potential in mice. Pre-treatment of cells with this nonapeptide did not block signal transduction through plasma membrane receptors for the following growth or differentiation factors: $\alpha$-melanotropin, NGF, and transforming growth factor type $\beta$.

Jensen (*Developmental Biol.* (1987) 120: 56-64), examined the potential of human neuroblastoma cell line SHSY5Y to differentiate in vitro after prolonged exposure to 7S NGF. SHSY5Y cells exposed to 7S NGF for periods exceeding five weeks and selected with aphidicolin closely resembled mature neurons as judged by several criteria. The treated and selected neurons survived for prolonged periods in culture in the presence of NGF. Human neuroblastoma SHSY5Y cultures were exposed to murine 7S NGF for five weeks and subsequently selected with aphidicolin for one week those cells were no longer mitotically active. It was pointed out that aphidicolin is a reversible inhibitor of $\alpha$DNA polymerase and therefore kills mitotically active cells with prolonged exposure.

Thus, aphidicolin was utilized by Jensen simply to kill mitotically active cells. The addition of aphidicolin during the second week of culture treatment is necessary as even a small population of mitotically active cells will quickly overgrow a mitotically quiescent culture. The aphidicolin selection step was only introduced to compensate for apparent variabilities in the timing of differentiation and for the small degree of phenotypic and/or genetic instability which appeared to exist within the undifferentiated SHSY5Y cells. Aphidicolin was not added to enhance differentiation.

Moreover, Jensen fails to mention, as disclosed by the present invention, that a sublethal dose of aphidicolin enhances the capacity of NGF to promote differentiation of neuroblastoma cells. Instead, Jensen used a high, lethal concentration (30 $\mu$M) to kill mitotically active cells.

Additionally, aphidicolin does not promote morphological changes in the absence of NGF. Jensen does point out that aphidicolin causes HeLa cells to accumulate in the $G_1$ stage of the cell cycle and suggests that aphidicolin thus may act synergistically with NGF to promote entry into $G_0$. Under similar conditions, retinoic acid also promoted certain aspects of a differentiated phenotype. Retinoic acidaphidicolin treated cultures exhibited similar morphological differentiation to the NGF treated cultures.

Although Jensen subjected neuroblastoma to a combination of NGF and aphidicolin, the dose of aphidicolin used and the time the aphidicolin was applied to the cells is distinct from the novel method. Furthermore, Jensen indicates that aphidicolin alone does not induce differentiation. Although there is a suggestion that aphidicolin may act synergistically with NGF to promote entry into $G_0$, there is no relation of entry into $G_0$ to differentiation. Moreover, Jensen does not mention that a sublethal dose of aphidicolin may enhance the capacity of NGF to promote differentiation of neuroblastoma cells.

Goretzki et al. (*Surgery* (1987) 102: 1035-1042) investigated whether sensitivity of human medullary thyroid carcinoma (hMTC) cells to chemotherapeutic drugs could be increased in vitro to initiate a more effective adjuvant chemotherapeutic approach for patients who undergo only palliative surgery. They report that NGF stimulated $^3$H-thymidine incorporation into hMTC cells according to dose and caused an enhanced cell proliferation in these cells up to threefold. Pre-incubation with NGF for 24 hours stimulated hMTC cells and made them more sensitive to cytotoxic therapy with doxorubicin. Stimulation of proliferation, i.e., hMTC and other APUD cells with NGF, enhanced the cytotoxicity of chemotherapeutic drugs to these cells. Therefore, Goretzki appears to teach away from the combination of a cytostatic or cytotoxic compound with NGF to enhance differentiation of cancer cells.

Cattaneo and McKay (*Nature* (1990) 347: 762-765) report that NGF controls the proliferation of neuronal precursors in a defined culture system of cells derived from the early embryonic brain. These cells proliferated in response to NGF, but only after they had been exposed to basic fibroblast growth factor. On withdrawal of NGF, the proliferative cells differentiated into neurons. It was indicated that, in combination with other growth factors, NGF regulates the proliferation and terminal differentiation of neuroethothelial cells. The authors suggest that NGF and other members of the NGF family might promote both the proliferation of neuronal precursors and the survival/differentiation of neurons derived from these precursors.

Chen et al. (*Cell Growth* and *Differentiation* (1990) 1: 79–85) examined a series of neuroblastoma and neuroepithelioma cell lines for NGF-induced neurite extension and NGF modulation of the expression of neuronal markers. The results indicated that three neuroblastoma cell lines with a neuronal morphology and lacking N-myc amplification extended neurites in response to 200 ng/ml of NGF. The authors conclude that NGF-induced differentiation is confined to a particular class of neural-related tumors, and, furthermore, differentiation for these cell lines is incomplete.

Unlike the articles discussed above, in the present invention, NGF and a pulse of aphidicolin were used at sublethal concentrations to induce efficient differentiation of SHSY5Y cells with little resulting toxicity. Under these conditions, the neuroblastoma cells cease to proliferate and instead extend long neurites. This is the first demonstration of such unexpected and synergistic effects of a neurotrophic factor and a cell cycle blocker. This invention provides a model system for the study of the coupling of cell proliferation and neuronal differentiation, as well as a novel method of treating neuroblastomas and other tumors.

SUMMARY OF THE INVENTION

While cytostatic compounds are presently used to treat cancer, it has been discovered that the effects of these compounds may be unexpectedly enhanced by simultaneous treatment with differentiation-inducing factors such as neurotrophic factors. Treatment of neuroblastoma cells with neurotrophic factors and an inhibitor of cell proliferation induces unexpected neuronal differentiation resulting in cells which do not proliferate and do not revert to tumor phenotypes. Furthermore, differentiated cells treated for prolonged periods of time with a neurotrophin become dependent on it for survival.

These discoveries have been exploited to develop novel methods and compositions for treatment of tumors. More particularly, the present invention provides methods for treating a neuroblastoma including contacting the neuroblastoma with a neurotrophic factor and less than a lethal dose of an inhibitor of cell proliferation for about 1 to 15 days; and then maintaining the neuroblastoma in contact with the neurotrophic factor for about 1 to 15 days. A sub-lethal dose is all that is required to prevent cell proliferation when the neuroblastoma is treated simultaneously with a neurotrophic factor. Contact with the neurotrophic factor and proliferation inhibitor is preferably for about 3 to 7 days, with 5 days being most preferred. Additional contact with the neurotrophic factor is preferably for about 3 to 5 days, with 4 days being most preferred.

As used herein, "differentiation-inducing factor" includes any molecule, or combination of molecules, which cause a cell to evolve from a simple state to a more complex form. For example, a differentiation-inducing factor may cause small, flat neuroblastoma cells to become extended and to develop neurite outgrowths. Neurotrophic factors are one type of cell differentiation-inducing factor. The term "neurotrophic factors" encompasses those molecules which induce a neuronal cell to differentiate and which include naturally derived molecules or synthetically or recombinantly produced analogs thereof. Preferable neurotrophic factors are the neurotropins, a family of proteins including nerve growth factor (NGF), brain-derived nerve growth factor (BDNF), neurotropin-3, and neurotropin-4, and synthetically or recombinantly produced analogs thereof.

The term "inhibitor of cell proliferation" encompasses any molecule which reduced the frequency of or stops cell division. These inhibitors may include known molecules or synthetically or recombinantly produced analogs thereof. Preferable cell proliferation inhibitors include aphidicolin in sub-lethal doses about 0.1 $\mu$M to 0.5 $\mu$M, hydroxyurea in sub-lethal doses of about 0.5 to 2.0 mM, and thymidine in sub-lethal doses of about 1.0 mM to 2.5 mM.

The invention also provides methods for eliminating neuroblastoma cells. This method involves contacting the neuroblastoma with a neurotrophic factor and less than a lethal dose of a cell proliferation inhibitor for about 1 to 15 days; maintaining the neuroblastoma in contact with the neurotrophic factor for greater than about 16 days; and then withholding the neurotrophic factor from the neuroblastoma. The neuroblastoma that becomes differentiated due to treatment with a neurotrophic factor and cell proliferation inhibitor becomes dependent on the neurotrophic factor if contact is maintained with the factor for greater than about 16 days after differentiation occurs. Thus, cessation of treatment with the neurotrophic factor results in cell death.

Additionally, this invention includes methods for inducing the remission of a neuroblastoma. In this method, the neuroblastoma is contacted with a neurotrophic factor and less than a lethal dose of an inhibitor of cell proliferation for about 1 to 15 days. The contacted neuroblastoma is then treated with the neurotrophic factor for an additional 1 to 15 days. Remission of the neuroblastoma results when the cells stop proliferating and differentiate.

In addition, the invention provides methods for inducing neuroblastoma differentiation including contacting the neuroblastoma with a neurotrophic factor and less than a lethal dose of an inhibitor of cell proliferation for about 1 to 15 days; and maintaining the neuroblastoma in contact with a neurotrophic factor. This method provides a culture of differentiated neuronal cells useful for drug testing.

The invention further provides compositions for inducing remission of a neuroblastoma including a neurotrophic factor and less than a lethal dose of an inhibitor of cell proliferation.

BRIEF DESCRIPTION OF THE DRAWINGS

The foregoing and other objects of this invention, the various features thereof, as well as the invention itself, may be more fully understood from the following description, when read together with the accompanying drawings, in which:

FIG. 2A, 0 ng/ml of NGF; FIG. 2B, 100 ng/ml of NGF; FIG. 2C, 0.3 $\mu$M aphidicolin and 100 ng/ml NGF for 5 days and then with NGF for 4 days. Bar=25 $\mu$m;

FIG. 4A shows control cells; FIG. 4B shows neuroblastoma cells treated with NGF for 6 days; and FIG. 4C shows neuroblastoma cells treated with NGF-aphidicolin for 6 days and NGF alone for 7 days;

FIGS. 5A–5D are immunofluorescence micrographs showing the expression of the neuronal cytoskeletal protein in control neuroblastoma cells stained with control MAb P3X63Ag8 (FIG. 5A); anti-MAP 1B (FIG. 5B); anti-MAP 1B staining of neuroblastoma cells treated with NGF for 7 days (FIG. 5C); and anti-MAP 1B staining of treated neuroblastoma cells with NGF-aphidicolin for 6 days and NGF alone for 7 days (FIG. 5D). Bar=25 μm;

FIG. 7A shows neuroblastoma cells treated with NGF and 2 mM thymidine for 5 days, and then NGF alone for 5 days. FIG. 7B shows neuroblastoma cells were treated with NGF and 1.5 mM hydroxyurea for 6 days, and then NGF alone for 7 days.

DESCRIPTION OF THE PREFERRED EMBODIMENTS

Figure 1:
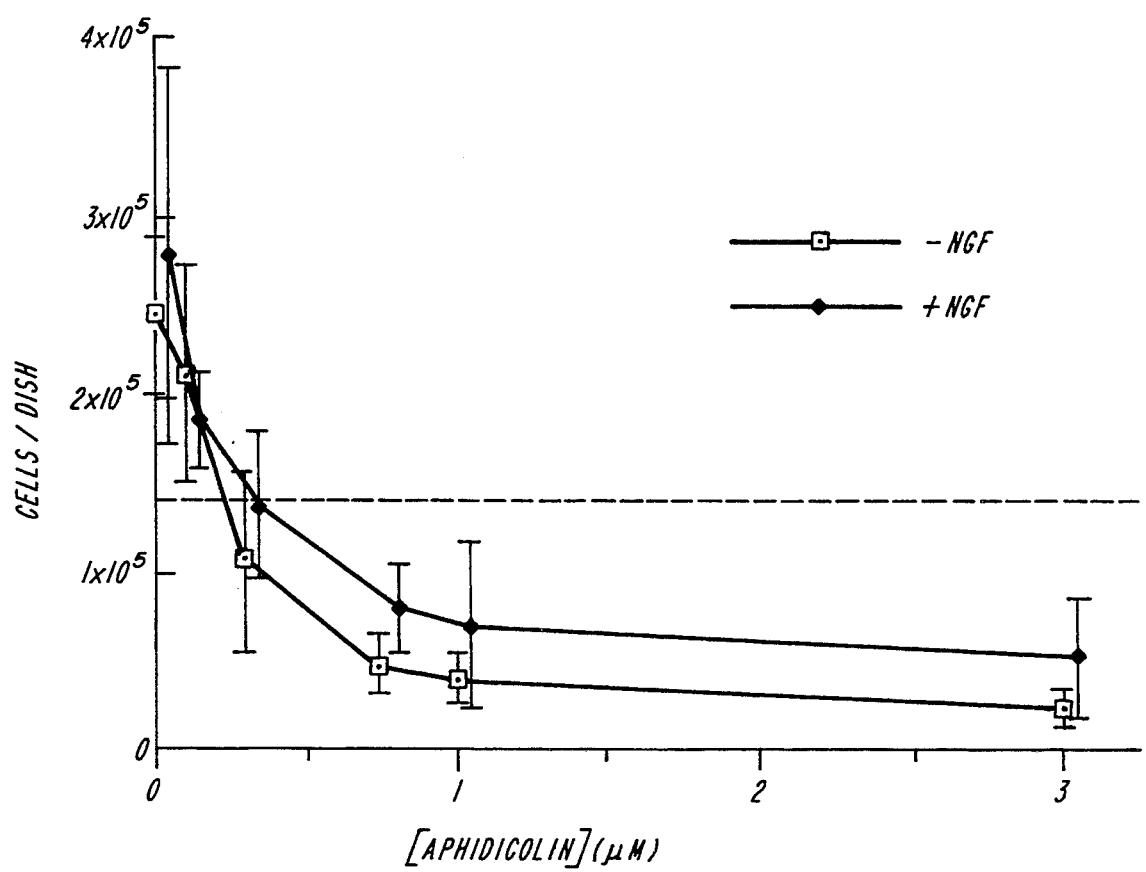
FIG. 1 is a graphic representation of the survival of cultured neuroblastoma cells with varied concentrations of aphidicolin in the presence and absence of NGF.

One skilled in the art will recognize that modifications may be made in the present invention without deviating from the spirit or scope of the invention. The invention is illustrated further by the following examples which are not to be construed as limiting the invention or scope of the specific procedures described herein.

I. MATERIALS AND METHODS

A. Cell Culture

A neuroblastoma cell line SHSY5Y was derived essentially according to the method of Biedler et al., 1978. Briefly, cells were grown in RPMI 1640 medium supplemented with 10% heat-inactivated fetal bovine serum, 2 mM glutamine and 100 μg/ml gentamycin. For differentiation studies, cells were plated ($1.5 \times 10^4 - 5 \times 10^5$ cells/dish) in 35-mm Primaria dishes.

Other useful human cell lines include the IMR32 (obtainable from the American Type Culture Collection, Rockville, Md., (CCL 127)) and LAN5 (obtainable from Dr. Robert Seeger, Childrens' Hospital, Los Angeles, Calif.) neuroblastoma cell lines which include the amplified N-myc oncogene, and the GICAN line (obtainable from Dr. Paolo Cornaglia-Ferraris, Institute of Giannina Gasline, Genoa, Italy) which, like SHSY5Y contains a single copy of N-myc.

B. Differentiation Factors and Cell Proliferation Inhibitors

Useful differentiation factors include those from the neurotrophin family (reviewed in Synder (1991) *Nature* 350: 195), including NGF, brain-derived NGF (BDNF), neurotrophin-3, and neurotrophin-4. Of course other neurotrophins and more broadly, other differentiation factors may be useful as well.

Useful cell proliferation inhibitors include aphidicolin, hydroxyurea, and thymidine. In one example, 100–200 ng/ml NGF (2.5 S from Bioproducts for Science) and/or varying concentrations of aphidicolin, thymidine or hydroxyurea (Sigma Chemical Co.) were added to the cultures every 2 days.

C. Antibodies

The following antibodies were used: anti-bromodeoxyuridine (BrdU) antibody conjugated with fluorescein (Boehringer Mannheim); mouse anti-microtubule-associated protein (MAP) 1A monoclonal antibodies (MAb) MAP1A-1 and MAP1A-2 (Bloom et al. (1984) *J. Cell Biol.* 98: 320–330), anti-MAP 1B MAbs MAP 1B-2 and MAP 1B-4 (Bloom et al. (1985) *Proc. Natl. Acad. Sci. USA* 82: 5404–5408; Luca et al. (1986) *Proc. Natl. Acad. Sci. USA* 83: 1006–1010), and anti-MAP 2 MAbs MAP 2-1, MAP 2-2, MAP 2-3, and MAP 2-4 (Dingus et al. (1991) *J. Biol. Chem.* 266: 18854–18860) were supplied by Dr. R. B. Vallee of the Worcester Foundation; mouse anti-tau MAb tau-1 (Boehringer Mannheim); mouse anti-synapsin Ia/b MAb M31 was supplied by Dr. L. J. DeGennaro (University of Massachusetts Medical College); anti-synapsin IIa/b MAb 19.31 supplied by Dr. A. J. Czernic (Rockefeller University) (Mandell et al. (1990) *Neuron* 5: 19–53); anti-synaptophysin MAb SY 38 (Boehringer Mannheim); anti-SV2 MAb from Dr. K. M. Buckley (Harvard Medical School) (Buckley and Kelly (1985) *J. Cell Biol.* 100: 1284–1294).

Fluorescine isothiocyanate-labeled goat anti-mouse IgG was from Fisher Biotech and fluorescein isothiocyanate-labeled goat anti-sheep IgG was from Sigma Chemical Co.

D. Immunofluorescence Microscopy

DNA synthesis by SHSY5Y cells was analyzed by immunofluorescence detection of BrdU incorporation, according to Hall and Landis (*Neuron* (1991) 6: 741–742). Cells grown on Primaria culture dishes were incubated for 17–24 hours (hrs) with 10 μg/ml of BrdU, washed with PBS, and fixed for 10 minutes (min) in methanol-5% acetic acid (−20° C). The cells were washed with PBS, the DNA was denatured with 2N HCl for 20 min, and the cells were washed with PBS. To reduce the volume of antibody needed, the culture dishes were painted with nail polish except for a coverslip size circle at the center of the dish. The cells were incubated for 1.5 hours with 100 μl anti-BrdU fluoresceinated antibody (20 μg/ml) with 0.5% Tween 20, 1% BSA in PBS. After washing in PBS, the unpainted region of the dish was covered with a coverslip, and the cells were examined with a Zeiss Axioplan microscope with a 25X neofluor objective. Images were photographed on Kodak TMAX 400 film.

For MAP immunocytochemistry, the cells were washed with phosphate buffered saline (PBS), fixed for 10 min in ethanol-5% acetic acid (−20° C.), and incubated with anti-MAP ascites (1:200) for 30 min.

For tau immunocytochemistry, the cells were fixed with 4% paraformaldehyde for 20 min. The cells were washed in PBS, permeabilized with 100% ethanol (−20° C.), incubated with 1% BSA for 5 min, and washed with PBS. The cells were incubated with MAb tau-I (5 μg/ml) for 30 min.

For synapsin immunocytochemistry, the cells were fixed with 4% paraformaldehyde for 20 minutes. Following fixation, the cells were incubated with 0.1% BSA and then with anti-synapsin Ia/b M31 ascites (1:500) or anti-synapsin IIa/b 19.31 ascites (1:100) for 30 minutes. For SV2 immunocytochemistry, the cells were fixed with 4% paraformaldehyde for 20 min. The cells were permeabilized with 100% ethanol (−20° C.), blocked with 0.1% BSA in PBS for 5 min, and incubated with anti-SV2 ascites (1:50 dilution with 0.1% BSA and 0.075% saponin) for 1 hr. For synaptophysin immunochemistry, the cells were fixed with 4% paraformaldehyde for 20 min, permeabilized with 100% ethanol (−20° C.), incubated with 0.1% BSA, and incubated with 2 μg/ml of SY38 MAb.

After labelling with the various primary antibodies, the cells were washed with PBS and incubated with the corresponding secondary antibodies. FITC-labeled goat anti-mouse IgG was used at a 1:100 dilution with PBS and FITC-labeled goat anti-sheep IgG was used at 1:50 dilution. After washing with PBS, the samples were mounted in citifluor glycerol.

E. RNA Isolation and Northern Blotting

Total RNA was isolated by the single-step method of Chomczynski and Sacchi (*Anal. Biochem.* (1987) 162: 156–159). The resulting RNA (10 μg/lane) was resolved by electrophoresis on a 1.0% agarose-formaldehyde gel, transferred to a Duralose membrane (Stratagene), and fixed with ultraviolet irradiation. The membranes were hybridized with $^{32}$P-dCTP-random primer-labeled 1.1-kb Sac I-Eco RI fragment of p1BHC-1 for MAP 1B (Hammarback et al. (1991) *Neuron* 7: 129–139), the 0.5-kb pJSN-1 probe for MAP2 (Dingus et al. (1991) *J. Biol. Chem.* 266: 18854–18860), the 0.4-kb pKK233-2 probe for tau (Lee et al. (1989) *Neuron* 2: 1615–1624), or the 1.7-kb p5E2 probe for synapsin I (Kilimann and DeGennaro (1985) *EMBO J.* 4: 1997–2002). The blots were washed twice with 2.0×SSC/0.1% SDS at room temperature followed by 2 washes with 2.0×SSC/0.1% SDS at 62° C. and one wash with 0.5×SSC/0.1% SDS at 62° C. The blots were exposed to Kodak XAR-5 film at −70° C. and then rehybridized with a 2.0-kb complementary DNA probe for β-actin (Gunning et al. (1983) *Mol. Cell Biol.* 3: 787–795). Scanning densitometry of autoradiograms was done with an LKB Ultroscan XL laser densitometer.

RESULTS

A. Differentiation of SHSY5Y Cells

SHSY5Y cells were plated on Primaria-treated plastic which enhances neuronal differentiation and tested various aphidicolin concentrations (0.1–3.0 μM) in the absence or presence of NGF. The cells were harvested, stained with trypan blue, and counted after four days of treatment. The results from three independent experiments are summarized in FIG. 1. Treatment of SHSY5Y cells with 0.3 μM aphidicolin stopped cell proliferation with little cell death; viability was greater than 90%. At higher concentrations of aphidicolin (1.0–3.0 μM) considerable cell death was observed in both the presence and absence of NGF.

Aphidicolin was removed from the medium after 5 days, and the SHSY5Y cells were treated with NGF alone. The results are shown in Table 1.

TABLE 1

NEURITE EXTENSION AND PROLIFERATION OF SHSY5Y CELLS

| Treatment | % Cells With Long Neurites[1] | % Cells Labelled With BrdU |
|---|---|---|
| None | 0 | 55–60 |
| +NGF | 5–10 | 50–60 |
| +NGF + 0.3 μM aphidicolin[2] | 60–70 | 1–2 |
| +NGF + 1.5 mM hydroxyurea[2] | 60–75 | 1–5 |
| +NGF + 2.0 mM thymidine[2] | 50–60 | 10–20 |
| +NGF + 0.5–2.0 μM nocodazole | N.A.[3] | N.A.[3] |
| +NGF + 0.01–1.0 μM colcemid | N.A.[3] | N.A.[3] |

[1]Cells were scored as positive if they displayed neurites longer than 5 cell diameters.
[2]Measurements of neurite extension and BrdU labelling were made after a 6 day exposure to NGF + the cell cycle blocker and then a 7 day treatment of NGF alone.
[3]N.A., not applicable. Some differentiated cells were observed following treatment, but because of the extensive cell toxicity caused by nocodazole and colcemid, these cultures were not analyzed further.

Figure 2A:
FIGS. 2A–2C are immunofluorescence micrographs showing the differentiation of cultured neuroblastoma cells in the presence of aphidicolin and/or NGF.
Figure 2B:
Figure 2C:
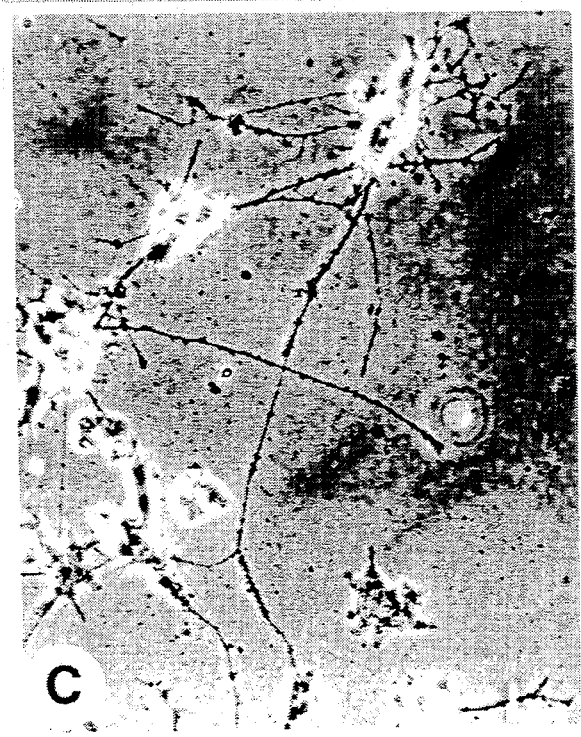

In the following week, neuronal differentiation was observed for cells previously treated with NGF and 0.1–3.0 μM aphidicolin. NGF alone induces neurite formation (FIG. 2B), but the resulting neurites are shorter and more branched than those displayed by the aphidicolin-NGF-treated cells (FIG. 2C). Also, the NGF-aphidicolin-treatment results in more rounded cell bodies. The optimum differentiation (neurite extension) with the least cell death was observed with 0.3 μM aphidicolin (FIG. 2C). Hence, this concentration (0.3 μM) of aphidicolin was used for all additional experiments.

There was no apparent affect of cell density on the neurite extension induced by NGF-aphidicolin-treatment. Similar results were obtained by plating 1.5×10$^4$ to 5×10$^5$ cells per dish.

Neurite extension was not observed for cells treated with aphidicolin alone. Significant neurite extension was not observed for cells treated with aphidicolin plus epidermal growth factor or basic fibroblast growth factor. Also, neuroblastoma cells treated with aphidicolin alone and then treated with NGF were indistinguishable from cells treated only with NGF. Hence, the neuroblastoma cells have to be treated simultaneously with NGF and aphidicolin to induce optimal neurite extension.

Figure 3A:
FIGS. 3A–3C are immunofluorescence micrographs showing the time course of neuroblastoma cell neurite extension in the presence of NGF and aphidicolin for 5 days and then with NGF alone for 1 day, (FIG. 3A); 4 days, (FIG. 3B); and 8 days, (FIG. 3C). Bar=25 μm.
Figure 3B:
Figure 3C:
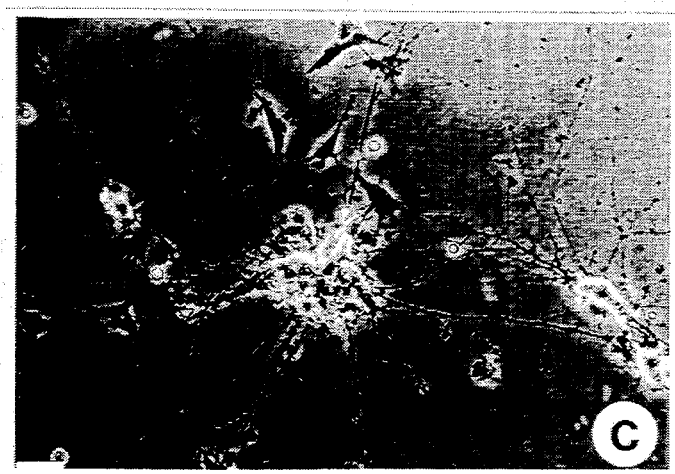

The time-course of differentiation suggests that the NGF-aphidicolin treatment induces a commitment to differentiation. Only about 6% of the neuroblastoma cells treated for 5 days with NGF-aphidicolin then 1 day with NGF displayed long neurites (See FIG. 3A). After 4 days of treatment with NGF, 60–70% of the cells assumed an altered morphology (FIG. 3B). The cell bodies were more rounded, and the cells extended neurites sometimes greater than 400 μm long. After 8 days of NGF treatment, aggregates of differentiated cell bodies were observed (FIG. 3C). If maintained in NGF, the cells with long neurites were stable for at least one month. Removal of NGF resulted in retraction of neurites and extensive cell death within 4–5 days. This is in sharp contrast to untreated cells which have no dependence on NGF. Thus differentiated cells dependent on NGF can be eliminated by cessation of NGF treatment.

Figure 4A:
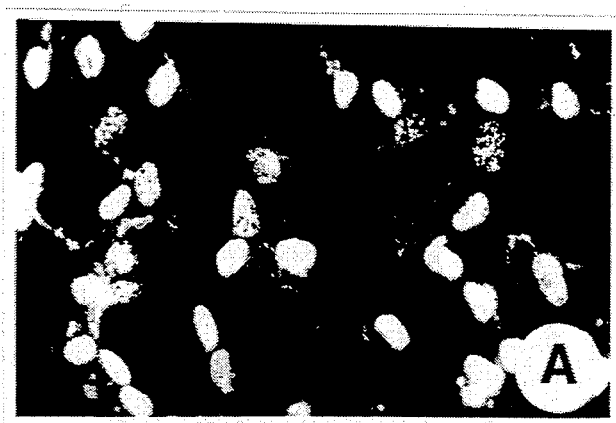
FIGS. 4A–4C are immunofluorescence micrographs showing the mitotic tendencies of cultured neuroblastoma cells labelled with BrdU after treatment with aphidicolin and/or NGF.
Figure 4B:
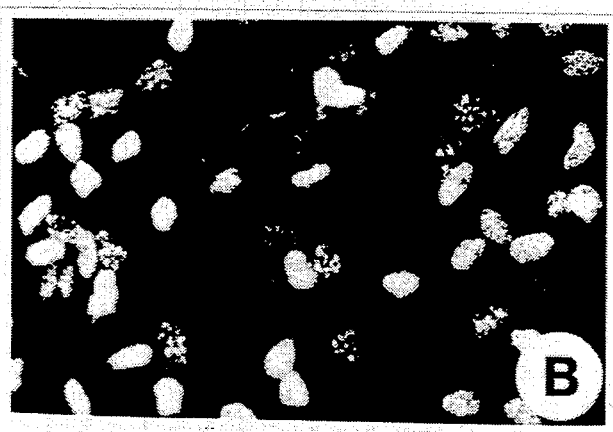
Figure 4C:
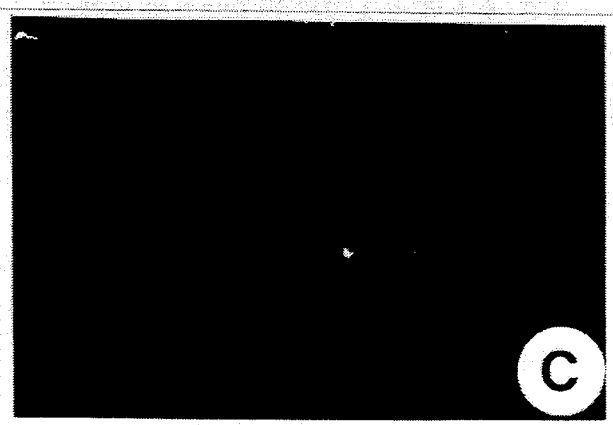

The cells with long neurites were not mitotic, as judged by incorporation of BrdU. SHSY5Y cells were labelled for 18 hours with BrdU and analyzed by immunofluorescence microscopy, as described in the Methods section above. The results are shown in FIG. 4. Control cells were intensely labelled with BrdU, and treatment with NGF alone did not significantly slow cell proliferation (FIG. 4B, Table 1). In contrast, very few SHSY5Y cells treated with aphidicolin and NGF followed by 7 days of NGF treatment were labelled (FIG. 4C). The few BrdU-positive cells did not display long neurites and instead resembled the parental SHSY5Y cells. These cells overgrew the cultures after 3–4 weeks, ending the experiment.

A second treatment of the mitotic cells with NGF-aphidicolin resulted in a differentiated culture indistinguishable from that observed for the parental cells. Hence, the few mitotic cells following NGF-aphidicolin treatment are not resistant to aphidicolin and probably arise due to the incomplete efficiency of the NGF-aphidicolin-treatment.

B. Expression of Neuronal Markers by SHSY5Y Cells

Figure 6:
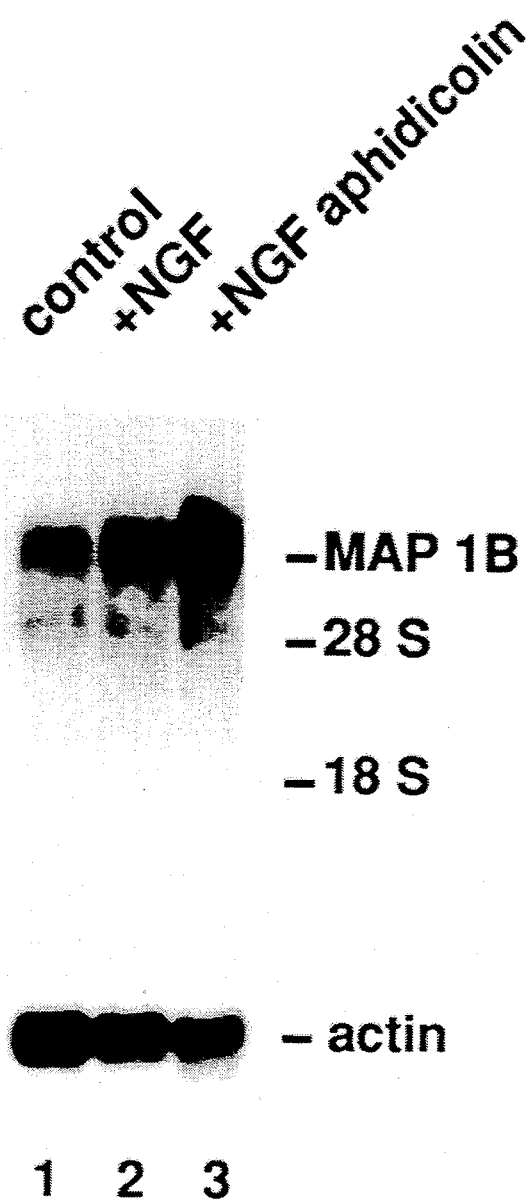
FIG. 6 is a photographic representation of a Northern blot of MAP 1B mRNA. Lane 1, control cells; lane 2, cells treated with NGF for 6 days; lane 3, NGF-aphidicolin treatment for 5 days and NGF treatment for 7 days.

Because of their importance in the regulation of neurite extension and cell proliferation, the expression of neuronal cytoskeletal proteins in control, NGF-treated, and NGF-aphidicolin-treated SHSY5Y cells was analyzed. The results are summarized in Table 2.

days (FIG. 6, line 3). Ethidium bromide staining of RNA prior to transfer, as well as rehybridization of filters with the 6-actin probe confirmed that the RNA was intact and that differences in MAP 1B mRNA levels could not be attributed to unequal loading. Treatment of SHSY5Y cells with aphidicolin alone did not upregulate MAP 1B mRNA or protein. The upregulation of MAP 1B mRNA in differentiated cells and the strong staining of all neurites with anti-MAP 1B antibody, suggest that MAP 1B plays an important role in neurite extension by SHSY5Y cells.

By Northern blotting, the MAP 2 mRNA was detected as a faint band at 9.0 kb (Table 2). However using a set of 4 MAbs which detect MAP 2, no protein was detected by immunofluorescence microscopy. Tau antigen was detected in the nucleoli of control and differentiated SHSY5Y cells (Table 2). The nucleolar staining for tau has been reported for other neuroblastoma cell lines and may be due to crossreactivity of this particular MAb with a tau-related protein. For NGF-aphidicolin-treated cells, staining of cell bodies and neurites for some cells (30–35%) was observed, but no upregulation of tau mRNA was detected.

The expression of antigens associated with synaptic vesicles was also analyzed. Synaptophysin, a putative synaptic vesicle Ca++ receptor and a clinical marker for neuroblastomas, was detected in SHSY5Y cells (Table 2). The immunofluorescence staining was enhanced in cells induced to differentiate with NGF-aphdicolin with about 10–15% of cells positive. SV2, a synaptic vesicle protein with unknown function, was

TABLE 2

| EXPRESSION OF NEURONAL MARKERS BY SHSY5Y CELLS | | | | |
|---|---|---|---|---|
| Marker | Control Cells | +NGF Cells | NGF-Aphidicolin Cells[1] | Localization |
| MAP 1A | N.D./+[2] | N.D./+ | N.D./+ | Cell body + neurites |
| MAP 1B | +/+ | +/+ | ++/++ | Cell body + neurites |
| MAP 2 | +/− | +/− | +/− | — |
| tau | +/− | +/± | +/+ | Cell body + nucleoli + some neutrites |
| synapto-physin | N.D./± | N.D./± | N.D./+ | Perinuclear |
| SV2 neurites | N.D./− | N.D./− | N.D./± | Perinuclear + some |
| synapsin I a/b | −/− | −/− | −/− | — |
| synapsin II a/b | N.D./− | N.D./− | N.D./− | — |

[1]The NGF-aphidicolin-treated cells were incubated with aphidicolin (0.3 μM) and NGF (200 ng/ml) and then with NGF alone for 5–10 days.
[2]N.D., not done. Data are given for Norther blotting/immunofluorescence microscopy. There experiments were qualitatively scored as follows: —, negative; ±, only weakly detected; +, easily detected; ++, intense signal.

The expression of MAP 1A is strong in all three culture conditions, and there was no apparent increase upon neuronal differentiation. As shown in FIG. 5D, immunostaining of MAP 1B was greatly enhanced in NGF-aphidicolin-treated cells. MAP 1B was detected in both the cell bodies and all of the long neurites (FIG. 5D).

FIG. 6 shows a Northern blot of MAP 1B mRNA. Total RNA was extracted from SHSY5Y cells, separated by agarose gel electrophoresis, transferred to a membrane, and hybridized with a MAP 1B probe. Based on the positions of ribosomal RNAs and marker RNAs, the MAP 1B mRNA is about 9.0 kb. The blot was stripped in low-ionic strength buffer and rehybridized with a probe for β-actin. The mRNA for MAP 1B was unregulated about 3-fold in cells treated for 5 days with NGF and aphidicolin and NGF treatment for 7 not detected in control and NGF-treated SHSY5Y cells. A small percentage (5–10%) of NGF-aphidicolin-treated cells were positive with staining of the cytoplasm and neurites. Synapsins Ia/b and IIa/b, which are thought to regulate synapse formation and to provide the cytoskeletal framework for the synaptic vesicles, were not detected (Table 2). As a positive control, NGF-treated PC12 cells were analyzed using the same conditions, and intense immunostaining for SV2 and synapsin Ia/b was detected. Hence, under conditions in which there is strong expression of axonal markers, expression of several critical synaptic antigens is heterogeneous or undetectable.

C. Effects of Other Inhibitors on Cell Proliferation

Figure 7A:
FIGS. 7A–7B are immunofluorescence micrographs showing the differentiation of neuroblastoma cells enhanced by thymidine and hydroxyurea.
Figure 7B:

The effects of other inhibitors of cell proliferation on SHSY5Y differentiation was tested using NGF in combination with thymidine or hydroxyurea instead of aphidicolin. The response of SHSY5Y cells to NGF and thymidine was similar to that described for NGF and aphidicolin, except that a slightly higher percent of cells were labelled with BrdU (FIG. 7A, Table 1). The response of SHSY5Y cells to NGF and hydroxyurea was similar to that for NGF and aphidicolin, except that the response was faster (FIG. 7B, Table 1). Neurites were evident for cells treated with NGF and hydroxyurea for 4 days, in contrast to NGF and aphidicolin-treated cells whose neurites were not evident until several days after the removal of aphidicolin (FIG. 3).

Neither thymidine nor hydroxyurea alone induced neurite extension. Also, in both cases, a similar sequence of morphologies was observed. Cells first extended neurites. See FIG. 7A which shows initial differentiation for cells treated with NGF and thymidine), and then at later times, the cell bodies became more rounded and formed clusters. See FIG. 7B which shows the later stage of differentiation for NGF and hydroxyurea-treated cells).

Nocodazole and colcemid which block the cell cycle at M phase were also tested. Treatment of SHSY5Y cells with these drugs resulted in considerable cell toxicity, although some of the surviving cells displayed long neurites.

The principal result of this study is that drugs which block cell proliferation and induced cell differentiation act synergistically to induce SHSY5Y cells to differentiate to a non-cancerous state. Since aphidicolin, hydroxyurea, and thymidine are chemically unrelated, these drugs are most likely acting by blocking the cell cycle and not by some uncharacterized side effect.

This system may provide a model for the coupling of cell proliferation and neuronal differentiation.

In an earlier study, SHSY5Y neuroblastoma cells were treated with NGF and 30 μM of aphidicolin and then with NGF alone (Jensen (1987) *Dev. Biol.* 120: 56–64). The resulting SHSY5Y cells were highly differentiated, postmitotic and dependent on NGF for survival. However, there was extensive cell death (>60%) and only a small fraction of the cells underwent terminal differentiation. In the present invention, the efficiency of differentiation was increased by using sublethal concentrations (0.3 μM) of aphidicolin. Thus, by using a sublethal does of cell proliferation inhibitor, the method of the invention provides for a large number of healthy, differentiated cells.

These resulting cells appear to be terminally differentiated, as judged by the following criteria: (1) the cells express neuronal differentiation markers and display a highly differentiated morphology; (2) the cells are not mitotic, as judged by BrdU labelling; (3) unlike the untreated or NGF-treated SHSY5Y cells, the NGF-aphidicolin-treated cells require NGF for survival. A caveat in the last criterion is that the differentiated SHSY5Y cells deprived of NGF die more slowly (4–5 days) than sympathetic neurons (1–2 days) (Martin et al. (1988) *J. Cell Biol.* 106: 829–844). Nonetheless, the dependency of the differentiated cells on NGF can be utilized in a method of treating neuroblastoma where it is desirable to eliminate the differentiated neuroblastoma cells.

Aphidicolin is required to stop cell proliferation for several potential reasons, even though NGF alone stops cell proliferation in PC12 cells (Greene and Tischler (1976) *Proc. Natl. Acad. Sci. USA* 73: 2424–2428). One possibility is that normal control of cell proliferation was lost during oncogenic transformation. For example, retinal cells transformed with SV40 T-antigen express neuronal markers and resemble mature retinal neurons, but are still mitotically active (Hammang et al. (1990) *Neuron* 4: 775–782). A second possibility is that the proliferation of the neuroblastic precursor cells from which neuroblastomas are derived is not sensitive to NGF. In fact, it has been reported that the proliferation of chick and rat sympathetic neuroblastic precursor cells is not affected by NGF even though NGF unregulated the amino acid metabolism of the rat cells (Ernsberger et al. (1989) *Neuron* 2: 1275–1284; DiCicco-Bloom et al. (1990) *J. Cell Biol.* 110: 2073–2086).

Dinsmore and Solomon (*Cell* (1991) 64: 817–826) have proposed that differentiation and cell proliferation are coupled through MAPs. In particular, they found that MAP 2 expression was required for cessation of cell proliferation of retinoic acid-treated embryonal carcinoma cells. After treatment with NGF-aphidicolin, SHSY5Y cells establish long, relatively unbranched neurites which contain MAP 1A and MAP 1B , and tau but lack MAP 2. Since MAP 2 is a dendritic marker and broad neurites were not observed with the characteristic morphology of dendrites, the lack of MAP 2 may reflect the axonal character of the neurites. Earlier studies suggest that MAP 1A, MAP 1B , MAP 2 and tau play a role in neurite extension and maintenance (reviewed in Vallee (1990)). The upregulation of MAP 1B mRNA in differentiated SHSY5Y cells and the strong immunostaining of neurites in the NGF-aphidicolin-treated cells suggest that, in this system, MAP 1B may be particularly important for neurite extension. cells.

Expression of synaptic markers was also analysed, and weak expression of synaptophysin and SV2 was detected. No expression of synapsin Ia/b and IIa/b which are thought to be critical for synapse formation, was found. Thiel et al. (1991) previously reported that proliferating neural cell lines, including SHSY5Y, express little or no synapsin Ia/b or IIa/b. Since synapsin Ia/b is expressed in most CNS and PNS neurons, it is unlikely that the SHSY5Y cells do not express it because they are differentiating into the wrong type of neuron. The lack of synapsin may reflect a general deficiency in the synaptic vesicles of human neuroblastoma cell lines. Even though neuroblastoma cells take up catecholamines from the medium via the sodium-dependent, reuptake protein, these cells lack vesicles which can concentrate and store the catecholamines. These results suggest that the mechanisms of regulation of axonal and synaptic markers differ and that neural tumors may lack a factor required for expression of synapsins but not for expression of axonal markers, such as MAP 1B.

The model suggested by these studies is that neuronal differentiation is triggered by two simultaneous signals: the cessation of cell proliferation and the presence of the appropriate neurotrophic factor.

From the foregoing, it will appreciated that although specific embodiments of the invention have been described herein for purposes of illustration, various modifications may be made without deviating from the spirit or scope of the invention.

What is claimed is:

1. A method for treating a cultured neuroblastoma cell comprising the steps of:
   (a) contacting the neuroblastoma cell with a neurotrophic factor and a sublethal dose of an inhibitor of cell proliferation selected from the group consisting of aphidicolin, hydroxyurea, and thymidine for about 1 to 15 days, the neurotrophic factor being nerve growth factor; and
   (b) maintaining the neuroblastoma cell in contact with the neurotrophic factor for about 1 to 15 days,
   wherein the inhibitor enhances neurotrophic factor-induced differentiation of the neuroblastoma cell into a neurite-extending neuron.

2. The method of claim 1, wherein the neuroblastoma cell is contacted with the neurotrophic factor and inhibitor of cell proliferation for about 3 to 7 days.

3. The method of claim 2, wherein the neuroblastoma cell is contacted with the neurotrophic factor and inhibitor of cell proliferation for about 5 days.

4. The method of claim 3, wherein the neuroblastoma cell is maintained in contact with the neurotrophic factor for about 3 to 5 days.

5. The method of claim 4, wherein the neuroblastoma cell is maintained in contact with the neurotrophic factor for about 4 days.

6. The method of claim 1, wherein the inhibitor of cell proliferation is aphidicolin.

7. The method of claim 6, wherein the sublethal dose of aphidicolin is from about 0.1 $\mu$M to about 0.5 $\mu$M.

8. The method of claim 7, wherein the sublethal dose of aphidicolin is about 0.3 $\mu$M.

9. The method of claim 1, wherein the inhibitor of cell proliferation is hydroxyurea.

10. The method of claim 9, wherein the sublethal dose of hydroxyurea is from 0.5 mM to about 2.0 mM.

11. The method of claim 10, wherein the sublethal dose of hydroxyurea is about 1.5 mM.

12. The method of claim 1, wherein the inhibitor of cell proliferation is thymidine.

13. The method of claim 12, wherein the sublethal dose of thymidine is from about 1.0 to about 2.5 mM.

14. The method of claim 13, wherein the sublethal dose of thymidine is from about 2.0 mM.

15. A method for treating a cultured neuroblastoma cell comprising the steps of:
   (a) contacting the cultured neuroblastoma cell with nerve growth factor and 0.3 $\mu$M aphidicolin for about 5 days; and
   (b) maintaining the cultured neuroblastoma cell in contact with nerve growth factor for about 4 days,
   wherein the inhibitor enhances neurotrophie factor-induced differentiation of the neuroblastoma cell into a neurite-extending neuron.

16. A method for inducing cultured neuroblastoma cell differentiation comprising the steps of:
   (a) contacting the neuroblastoma cell with a neurotrophic factor and a sublethal dose of an inhibitor of cell proliferation selected from the group consisting of aphidicolin, hydroxyurea, and thymidine for about 1 to 15 days, the neurotrophic factor being nerve growth factor; and
   (b) maintaining the neuroblastoma cell in contact with the neurotrophic factor,
   wherein the inhibitor enhances neurotrophic factor-induced differentiation of the neuroblastoma cell into a neurite-extending neuron.

17. A composition for treating a cultured neuroblastoma cell comprising a neurotrophic factor and sublethal dose of an inhibitor of cell proliferation, the neurotrophic factor being nerve growth factor, and the inhibitor being selected from the group consisting of aphidicolin, hydroxyurea, and thymidine, the inhibitor having the ability to enhance neurotrophic factor-induced differentiation of the neuroblastoma cell into a neurite-extending neuron.

* * * * *